United States Patent [19]

Duffett

[11] Plant 5,226

[45] May 1, 1984

[54] CHRYSANTHEMUM PLANT NAMED YELLOW CAMBRIA

[75] Inventor: William E. Duffett, Salinas, Calif.

[73] Assignee: Yoder Brothers, Inc., Barberton, Ohio

[21] Appl. No.: 413,508

[22] Filed: Aug. 31, 1982

[51] Int. Cl.[3] ..... A01H 5/00

[52] U.S. Cl. ..... Plt./78

[58] Field of Search ..... Plt./74–77

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant named Yellow Cambria characterized by the combined characteristics of flat capitulum form; spider capitulum type; yellow ray floret color; diameter across face of capitulum ranging from 175 to 225 mm. at maturity; uniform nine (9) week photoperiodic flowering response to short days; tall 90 to 95 cm. plant height when grown single stem with no long days and a low temperature tolerance of 13° C. (55° F.) for initiation and development under controlled short days with a continuous dark period of 12 to 14 hours.

3 Drawing Figures

The present invention comprises a new and distinct cultivar of *Chrysanthemum morifolium,* Ramat., hereinafter referred to by the cultivar name Yellow Cambria.

Yellow Cambria is an induced mutation from an ivory white seedling disclosed under the cultivar name of Cambria, U.S. Plant Pat. No. 4,473. The planned mutation induction program had the objective of creating clear yellow ray floret color while retaining all other traits of the parent cultivar.

Yellow Cambria was discovered and selected as one flowering plant within a population of plants propagated from stock plants which had been irradiated as cuttings with an X-ray source of 1800 rads by William E. Duffett on Jan. 5, 1979 in a controlled environment in Salinas, Calif.

The first act of asexual reproduction of Yellow Cambria was accomplished when vegetative cuttings were taken from the initial selection in April, 1979 in a controlled environment in Salinas, Calif. by a technician working under formulations established and supervised by William E. Duffett.

Horticultural examination of selected units initiated October, 1980 has demonstrated that the combination of characteristics as herein disclosed for Yellow Cambria are firmly fixed and are retained through successive generations of asexual reproduction.

Yellow Cambria has not been observed under all possible environmental conditions. The phenotype may vary significantly with variations in environment such as temperature, light intensity, and day length. The following observations, measurements and comparisons describe plants grown in Salinas, Calif. under greenhouse conditions which approximate those generally used in commercial practice.

The following traits have been repeatedly observed and are determined to be basic characteristics of Yellow Cambria which in combination distinguish this chyrsanthemum as a new and distinct cultivar:

1. flat capitulum form;
2. spider capitulum type;
3. yellow ray floret color with minimum color oxidation;
4. diameter across face of capitulum ranging from 175 to 225 mm. at maturity;

5. uniform nine (9) week photoperiodic flowering response to short days;
6. tall plant height (requiring no long day weeks prior to short days to attain a flowered plant height of 80 to 90 cm. for May through October flowerings); and
7. low temperature tolerance of 13° C. (55° F.) for initiation and development when grown in single stem cut standard programs with a continuous dark period of 12 to 14 hours.

The accompanying photographic drawings show typical inflorescence and foliage characteristics of Yellow Cambria, with the colors being as nearly true as possible with illustrations of this type. Sheet 1 is a color photograph of Yellow Cambria grown as a single stem cut spider. Sheet 2 is a black and white photograph showing the leaves of Yellow Cambria at three stages of growth. Sheet 3 is a black and white photograph of three views of the inflorescence of Yellow Cambria.

Of the many commercial cultivars known to the present inventor, the most similar in comparison to Yellow Cambria is Super Yellow. Reference is made to attached Chart A which compares certain characteristics of Yellow Cambria to those same characteristics of Super Yellow.

In comparison to Super Yellow, Yellow Cambria has no bronzing coloration of ray florets with a cool finish (below 60° night temperatures), with superior color retention and a slower rate of oxidation; it has a larger diameter across the face of the capitulum by 25 to 50 mm., and taller plant height by approximately 20 cm.; it has similar capitulum form, type and response to short days. At temperatures of 13° C. (55° F.), Yellow Cambria will initiate and develop its buds uniformly. Super Yellow under the same environment responds nonuniformly.

In the following description, color references are made to The Royal Horticultural Society Color Chart. The color values were determined between 10:00 and 10:30 A.M. on July 26, 1982 under 150 foot-candle light intensity at Salinas, Calif.

CLASSIFICATION

Botanical: *Chrysanthemum morifolium,* Ramat., cv Yellow Cambria.

Commercial: Cut Yellow Spider.

INFLORESCENCE

A. Capitulum:

*Form.*—Flat.

*Type.*—Spider.

*Diameter across face.*—175 to 225 mm.

B. Corolla of ray florets:

*Color (general tonality from a distance of three meters).*—Yellow.

*Color (abaxial).*—5A oxidizing to 5C.

*Color (adaxial).*—9C oxidizing to 9D.

C. Corolla of disc florets:

*Color (mature).*—6D.

*Color (immature).*—154B.

D. Reproductive organs:

*Androecium.*—Present disc florets only; scant to few; scant pollen.

*Gynoecium.*—Present both ray and disc florets.

PLANT

A. General appearance:

*Height.*—Tall, 90 to 95 cm., as a flowering plant from a rooted cutting, with no long days for May through October flowerings and maintaining a minimum nightly 12 to 14 hour continuous dark period.

B. Foliage:

*Color (abaxial).*—147A.

*Color (adaxial).*—147B.

*Shape.*—Deeply lobed and coarsely serrated.

CHART A

COMPARISON OF YELLOW CAMBRIA AND SUPER YELLOW

| CULTIVAR | RAY FLORET COLOR | CAPITULUM FORM AND TYPE |
|---|---|---|
| YELLOW CAMBRIA | YELLOW | FLAT SPIDER |
| SUPER YELLOW | YELLOW TINGED BRONZE | FLAT SPIDER |

| CULTIVAR | DIAMETER ACROSS FACE OF CAPITULUM | PLANT HEIGHT | FLOWER RESPONSE PERIOD |
|---|---|---|---|
| YELLOW CAMBRIA | 175 to 225 mm. | TALL 90 to 95 cm. | 9 weeks |
| SUPER YELLOW | 150 to 175 mm. | SHORT 70 to 80 cm. | 9 weeks |

COMPARISONS MADE OF PLANTS GROWN AS SINGLE STEM CUT SPIDERS WITH NO LONG DAYS IN SALINAS, CALIFORNIA

I claim:

1. A new and distinct plant of *Chrysanthemum morifolium,* Ramat., known by the cultivar name of Yellow Cambria, as described and illustrated, and particularly characterized as to uniqueness by the combined characteristics of flat capitulum form; spider capitulum type; yellow ray floret color; diameter across face of capitulum ranging from 175 to 225 mm. at maturity; uniform nine (9) week flowering response; tall 90 to 95 cm. plant height when grown single stem with no long days and a low temperature tolerance of 13° C. (55° F.) for initiation and development under controlled short days with a continuous dark period of 12 to 14 hours.

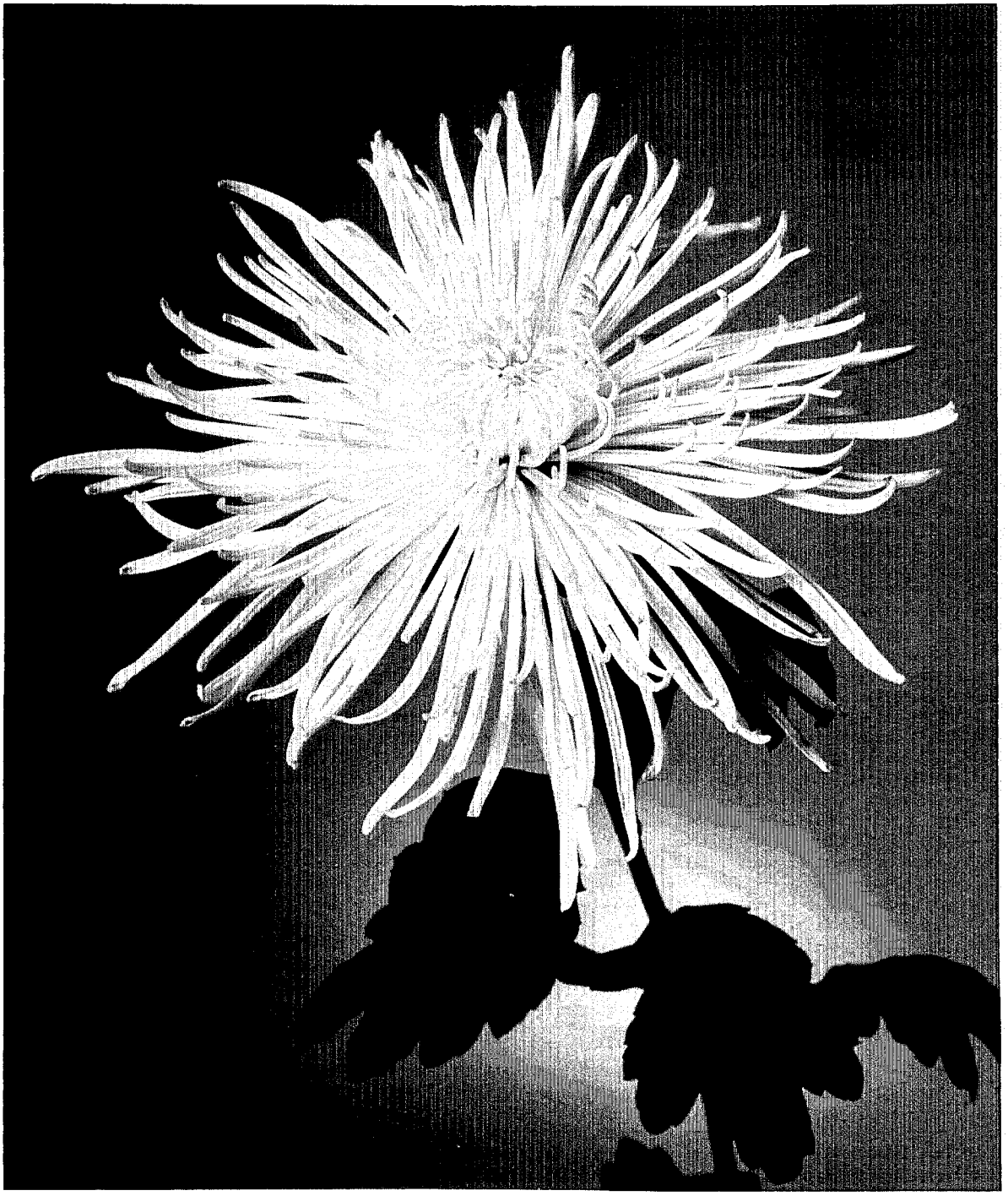

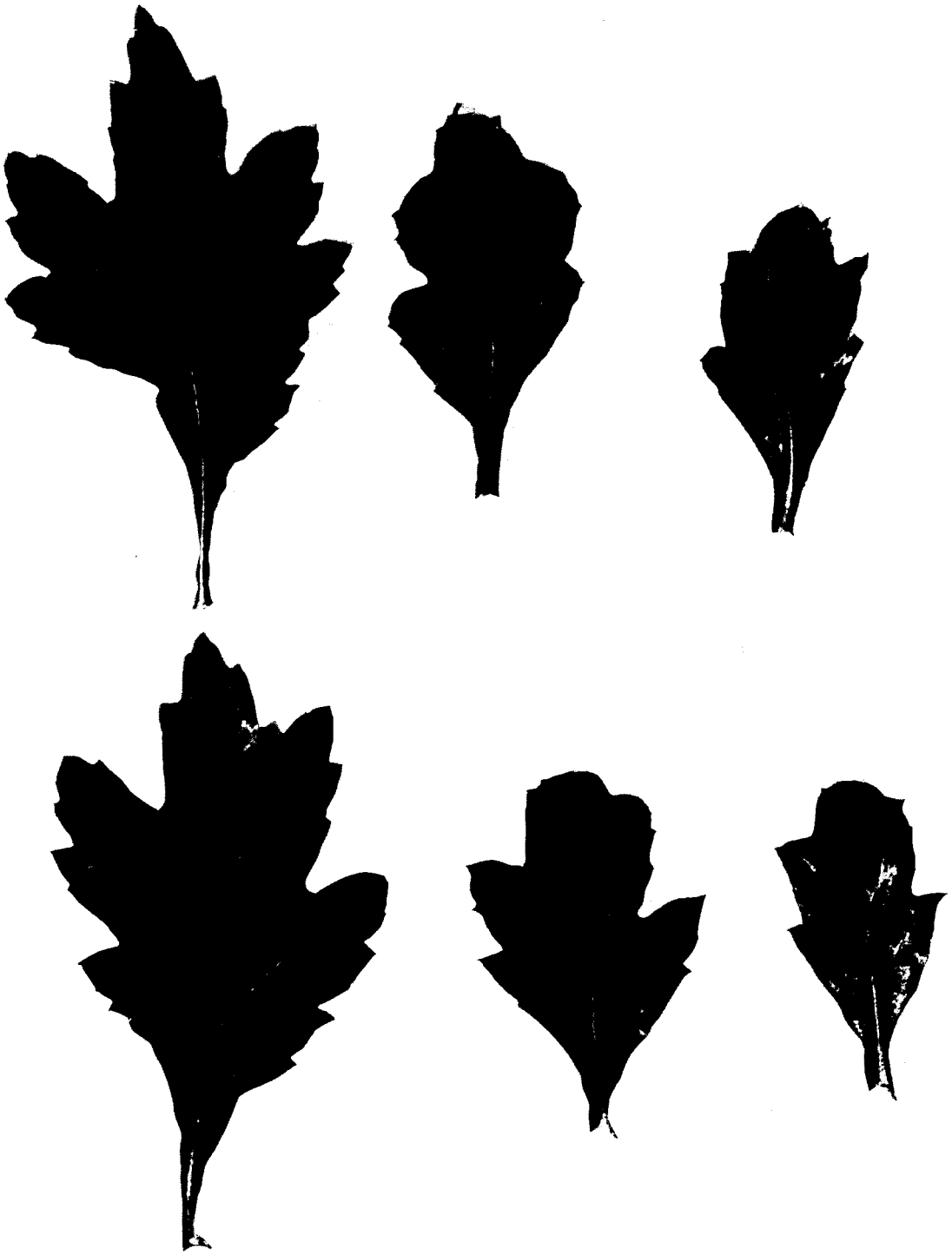

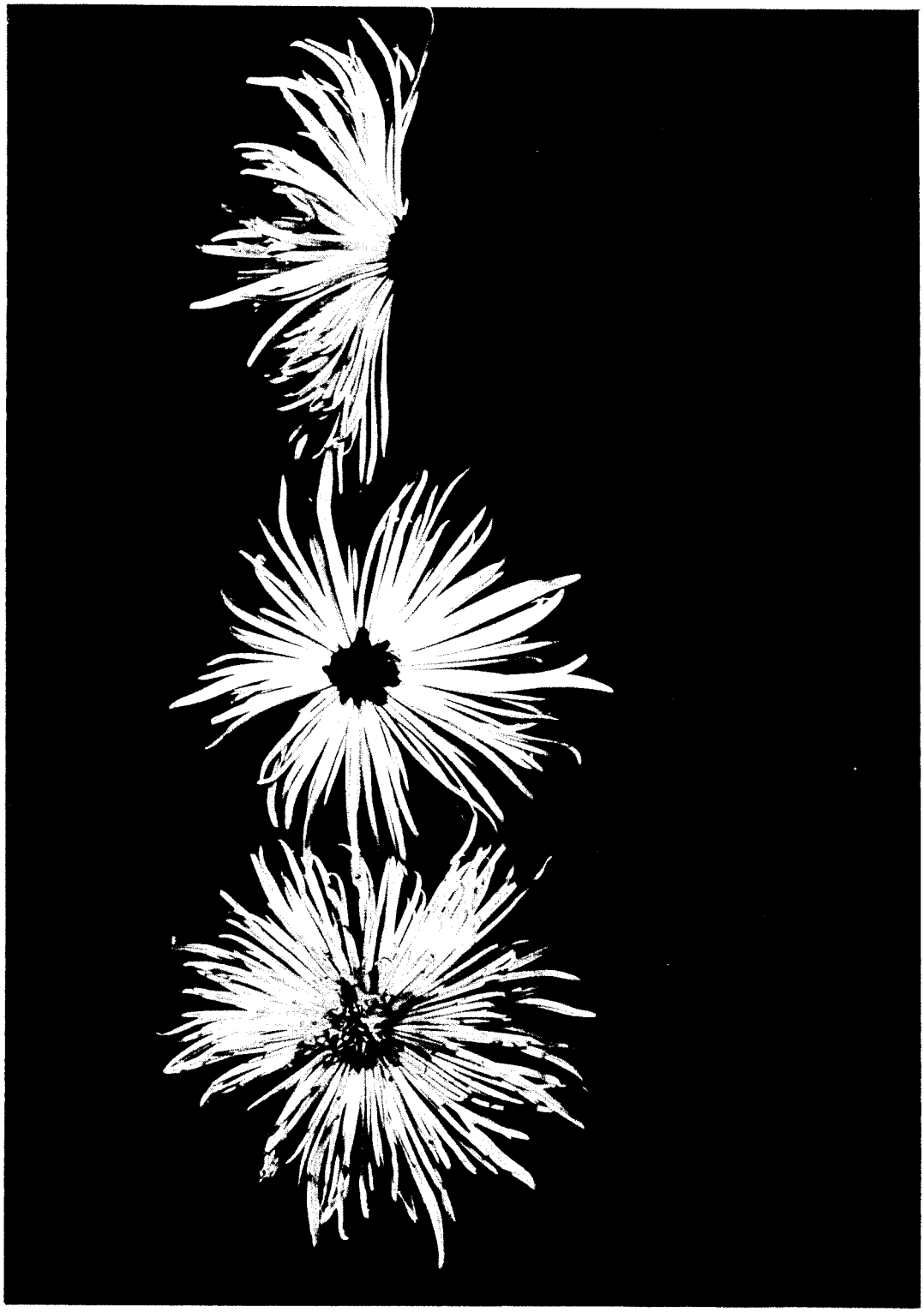

* * * * *